United States Patent
Ramee et al.

(12) 
(10) Patent No.: US 6,203,561 B1
(45) Date of Patent: Mar. 20, 2001

(54) INTEGRATED VASCULAR DEVICE HAVING THROMBECTOMY ELEMENT AND VASCULAR FILTER AND METHODS OF USE

(75) Inventors: Stephen Ramee, New Orleans, LA (US); Farhad Khosravi, San Mateo, CA (US); L. N. Hopkins, Buffalo, NY (US)

(73) Assignee: Incept LLC, San Mateo, CA (US)

( * ) Notice: Subject to any disclaimer, the term of this patent is extended or adjusted under 35 U.S.C. 154(b) by 0 days.

(21) Appl. No.: 09/470,681

(22) Filed: Dec. 23, 1999

Related U.S. Application Data

(63) Continuation-in-part of application No. 09/364,064, filed on Jul. 30, 1999.

(51) Int. Cl.[7] .................................................. A61M 29/00
(52) U.S. Cl. .......................................... 606/200; 606/194
(58) Field of Search .................................. 606/200, 191, 606/194

(56) References Cited

U.S. PATENT DOCUMENTS

| | | | |
|---|---|---|---|
| 3,592,186 | 7/1971 | Oster | 128/2 R |
| 3,683,904 | 8/1972 | Forster | 128/127 |
| 3,952,747 | 4/1976 | Kimmell, Jr. | 128/303 R |
| 3,996,938 | 12/1976 | Clark, III | 128/348 |
| 4,046,150 | 9/1977 | Schwartz et al. | 128/328 |
| 4,662,885 | 5/1987 | DiPisa, Jr. | 623/12 |
| 4,705,517 | 11/1987 | DiPisa, Jr. | 623/12 |
| 4,706,671 | 11/1987 | Weinrib | 128/348 |
| 4,723,549 | 2/1988 | Wholey et al. | 128/344 |
| 4,790,812 | 12/1988 | Hawkins, Jr. et al. | 604/22 |

(List continued on next page.)

FOREIGN PATENT DOCUMENTS

| | | | |
|---|---|---|---|
| 0 427 429 A1 | 5/1991 | (EP) | A61M/25/10 |
| 0 655 228 A1 | 11/1994 | (EP) | A61F/2/02 |
| 0 737 450 A1 | 10/1996 | (EP) | A61F/2/01 |
| 0 743 046 A1 | 11/1996 | (EP) | A61F/2/01 |
| 0 759 287 A1 | 2/1997 | (EP) | A61F/2/01 |
| 0 771 549 A2 | 5/1997 | (EP) | A61F/2/01 |
| 0 784 988 A1 | 7/1997 | (EP) | A61M/5/165 |
| 0 852 132 A1 | 7/1998 | (EP) | A61F/2/01 |
| 2 020 557 | 11/1979 | (GB) | A61B/17/50 |
| WO 94/14389 | 7/1994 | (WO) | A61F/2/02 |

(List continued on next page.)

OTHER PUBLICATIONS

Wholey, Mark H. et al., "PTA and Stents in the Treatment of Extracranial Circulation," *The Journal of Invasive Cardiology: vol. 8/Supplement E*, Health Management Publications, Inc., 1996, pp. 25E–30E.

Fadali, A. Moneim, "A filtering device for the prevention of particulate embolization during the course of cardiac surgery", *Surgery*, vol. 64(3), pp. 634–639 (Sep. 1968).

*Primary Examiner*—Gary Jackson
(74) *Attorney, Agent, or Firm*—Fish & Neave; Nicola A. Pisano

(57) ABSTRACT

Apparatus and methods are provided for use in removing thrombus from a vessel, wherein a vascular device comprises an thrombectomy element for excising or ablating thrombus and a vascular filter for capturing emboli generated during removal of the thrombus. The vascular filter comprises a support hoop having an articulation region connected near a distal end of a guide wire, and a blood permeable sac affixed to the support hoop so that the support hoop forms a mouth of the blood permeable sac. In a preferred embodiment, the thrombectomy element comprises a second support hoop and blood permeable sac attached to the guide wire proximal of the vascular filter support hoop.

22 Claims, 4 Drawing Sheets

U.S. PATENT DOCUMENTS

| | | | |
|---|---|---|---|
| 4,794,928 | 1/1989 | Kletschka | 128/344 |
| 4,807,626 | 2/1989 | McGirr | 128/328 |
| 4,873,978 | 10/1989 | Ginsburg | 128/345 |
| 4,921,478 | 5/1990 | Solano et al. | 604/53 |
| 4,921,484 | 5/1990 | Hillstead | 604/104 |
| 4,926,858 | 5/1990 | Gifford et al. | 606/159 |
| 4,969,891 | 11/1990 | Gewertz | 606/200 |
| 4,998,539 | 3/1991 | Delsanti | 128/898 |
| 5,002,560 | 3/1991 | Machold et al. | 606/198 |
| 5,011,488 | 4/1991 | Ginsburg | 606/159 |
| 5,053,008 | 10/1991 | Bajaj | 604/104 |
| 5,071,407 | 12/1991 | Termin et al. | 604/104 |
| 5,102,415 | 4/1992 | Guenther et al. | 606/159 |
| 5,108,419 | 4/1992 | Reger et al. | 606/200 |
| 5,133,733 | 7/1992 | Rasmussen et al. | 606/200 |
| 5,171,233 | 12/1992 | Amplatz et al. | 604/281 |
| 5,329,942 | 7/1994 | Gunther et al. | 128/898 |
| 5,354,310 | 10/1994 | Garnic et al. | 606/198 |
| 5,370,657 | 12/1994 | Irie | 606/200 |
| 5,383,887 | 1/1995 | Nadal | 606/200 |
| 5,415,630 | 5/1995 | Gory et al. | 604/53 |
| 5,421,832 | 6/1995 | Lefebvre | 604/53 |
| 5,456,667 | 10/1995 | Ham et al. | 604/107 |
| 5,476,104 | 12/1995 | Sheahon | 128/757 |
| 5,549,626 | 8/1996 | Miller et al. | 606/200 |
| 5,658,296 | 8/1997 | Bates et al. | 606/127 |
| 5,662,671 | 9/1997 | Barbut et al. | 606/170 |
| 5,669,933 | 9/1997 | Simon et al. | 600/200 |
| 5,695,519 | 12/1997 | Summers et al. | 606/200 |
| 5,746,758 | 5/1998 | Nordgren et al. | 606/159 |
| 5,769,816 | 6/1998 | Barbut et al. | 604/96 |
| 5,779,716 | 7/1998 | Cano et al. | 606/114 |
| 5,792,300 | 8/1998 | Inderbitzen et al. | 156/244.13 |
| 5,795,322 | 8/1998 | Boudewijn | 604/22 |
| 5,797,952 | 8/1998 | Klein | 606/198 |
| 5,800,457 | 9/1998 | Gelbfish | 606/200 |
| 5,800,525 | 9/1998 | Bachinski et al. | 623/1 |
| 5,814,064 | 9/1998 | Daniel et al. | 606/200 |
| 5,817,102 | 10/1998 | Johnson et al. | 606/108 |
| 5,827,324 | 10/1998 | Cassell et al. | 606/200 |
| 5,833,644 | 11/1998 | Zadno-Azizi et al. | 604/52 |
| 5,833,650 | 11/1998 | Imran | 604/53 |
| 5,846,260 | 12/1998 | Maahs | 606/200 |
| 5,876,367 | 3/1999 | Kaganov et al. | 604/8 |
| 5,893,867 | 4/1999 | Bagaoisan et al. | 606/198 |
| 5,895,399 | 4/1999 | Barbut et al. | 606/159 |
| 5,954,745 | 9/1999 | Gertler et al. | 606/200 |

FOREIGN PATENT DOCUMENTS

| | | | |
|---|---|---|---|
| WO 96/01591 | 1/1996 | (WO) | A61B/17/22 |
| WO 97/27808 | 8/1997 | (WO) | A61B/17/22 |
| WO 97/42879 | 11/1997 | (WO) | A61B/17/00 |
| WO 98/23322 | 6/1998 | (WO) | A61M/29/00 |
| WO 98/33443 | 8/1998 | (WO) | A61B/17/22 |
| WO 98/34673 | 8/1998 | (WO) | A61M/31/00 |
| WO 98/36786 | 8/1998 | (WO) | A61M/5/32 |
| WO 98/38920 | 9/1998 | (WO) | A61B/17/22 |
| WO 98/38929 | 9/1998 | (WO) | A61B/17/00 |
| WO 98/39053 | 9/1998 | (WO) | A61M/29/00 |
| WO 98/46297 | 10/1998 | (WO) | A61M/29/00 |
| WO 98/47447 | 10/1998 | (WO) | A61F/2/06 |
| WO 98/50103 | 11/1998 | (WO) | A61M/29/00 |
| WO 98/51237 | 11/1998 | (WO) | A61F/2/01 |
| WO 98/55175 | 12/1998 | (WO) | A61M/29/00 |
| WO 99/09895 | 3/1999 | (WO) | A61B/17/12 |
| WO 99/23976 | 5/1999 | (WO) | A61F/2/01 |

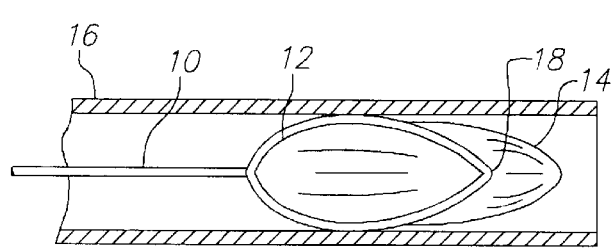
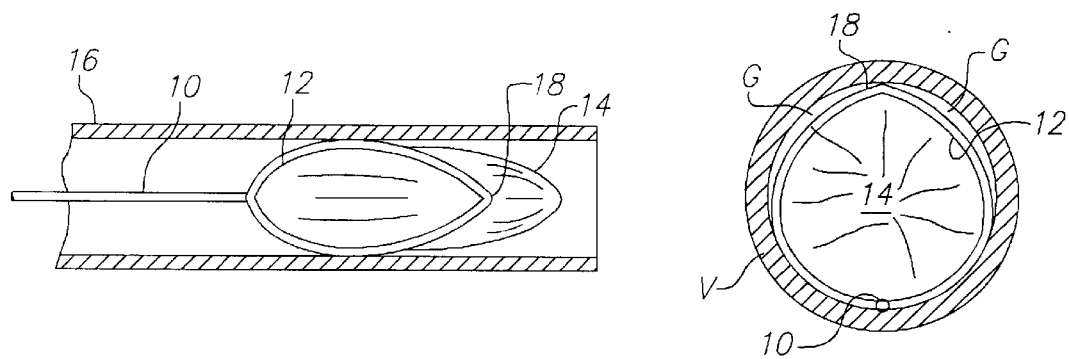
FIG. 1A (PRIOR ART)
FIG. 1B (PRIOR ART)
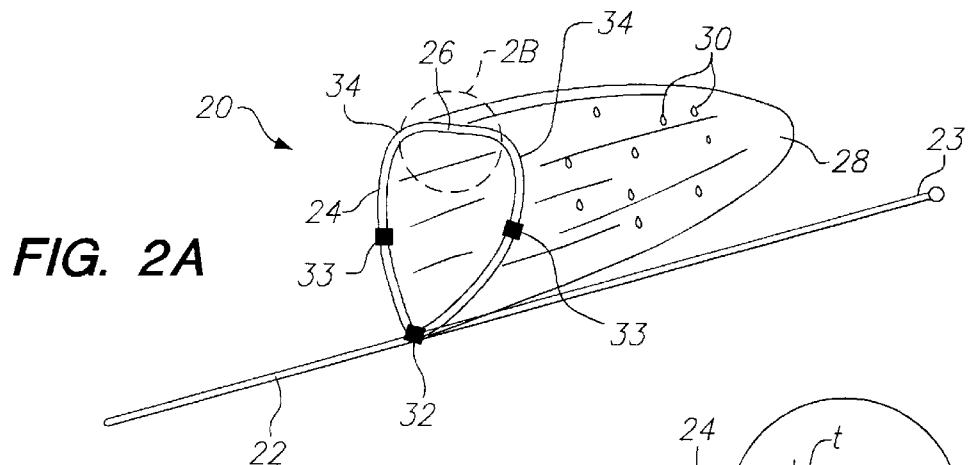
FIG. 2A
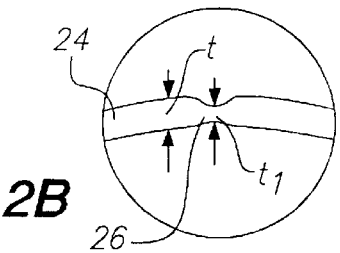
FIG. 2B
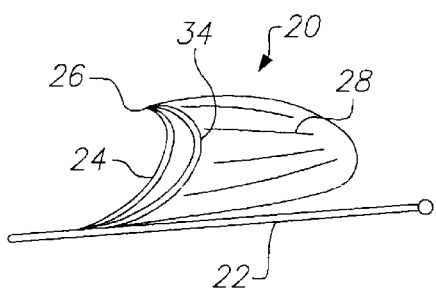
FIG. 3
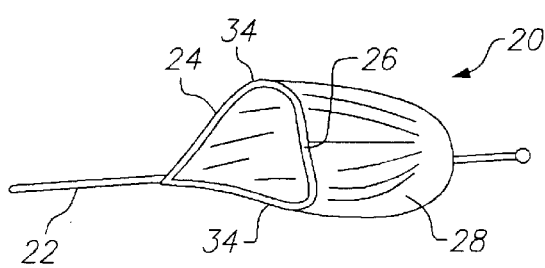
FIG. 4

INTEGRATED VASCULAR DEVICE HAVING THROMBECTOMY ELEMENT AND VASCULAR FILTER AND METHODS OF USE

REFERENCE TO RELATED APPLICATIONS

This application is a continuation-in-part of U.S. patent application Ser. No. 09/364,064 filed Jul. 30, 1999.

FIELD OF THE INVENTION

The present invention relates to apparatus and methods for removing thrombus from within a vascular system and filtering emboli generated by the procedure. More particularly, the present invention provides a low profile self-expanding vascular device with thrombectomy element and filter useful for the removal of thrombus and for capturing emboli generated during the thrombectomy procedure.

BACKGROUND OF THE INVENTION

Many percutaneous procedures for the removal of thrombus have been proposed. However, the procedures often dislodge material from the vessel walls. This dislodged material, known as emboli, enters the bloodstream, and may be large enough to occlude smaller downstream vessels, potentially blocking blood flow to tissue. The resulting ischemia poses a serious threat to the health or life of a patient if the blockage occurs in critical tissue, such as the heart, lungs, or brain.

Numerous previously known methods and apparatus have been proposed to reduce the risk of embolism. U.S. Pat. No. 5,833,644 to Zadno-Azizi et al., for example, describes the use of a balloon-tipped catheter to temporarily occlude flow through a vessel from which a stenosis is to be removed. Stenotic material removed during a treatment procedure is evacuated from the vessel before the flow of blood is restored. A drawback of such previously known systems, however, is that occlusion of antegrade flow through the vessel may result in damage to the tissue normally fed by the blocked vessel.

U.S. Pat. No. 5,814,064 to Daniel et al. describes an emboli filter system having a radially expandable mesh filter disposed on the distal end of a guide wire. The filter is deployed distal to a region of stenosis, and any interventional devices, such as an angioplasty balloon or stent delivery system, are advanced along the guide wire. The filter is designed to capture emboli generated during treatment of the stenosis while permitting blood to flow through the filter. Similar filter systems are described in U.S. Pat. No. 4,723,549 to Wholey et al. and U.S. Pat. No. 5,827,324 to Cassell et al.

One disadvantage of radially expandable filter systems such as described in the foregoing patents is the relative complexity of the devices, which typically comprise numerous parts. Connecting more than a minimal number of such parts to a guide wire generally reduces the ability of the guide wire to negotiate tortuous anatomy and increases the profile of the device in its delivery configuration. Consequently, it may be difficult or impossible to use such devices in small diameter vessels such as are commonly found in the carotid artery and cerebral vasculature. Moreover, such filter devices are generally incapable of preventing material from escaping from the filter during the process of collapsing the filter for removal.

International Publication No. WO 98/39053 describes a filter system comprising an elongated member, a radially expandable hoop and a cone-shaped basket. The hoop is affixed to the elongated member, and the cone-shaped basket is attached to the hoop and the elongated member so that the hoop forms the mouth of the basket. The filter system includes a specially configured delivery catheter that retains the mouth of the basket in a radially retracted position during delivery.

While the filter system described in the foregoing International Publication reduces the number of components used to deploy the cone-shaped basket, compared to the radial strut-type filter elements described hereinabove, it too has drawbacks. Chief among these, it is expected that it will be difficult to reduce the diameter of the radially expandable hoop to its retracted position. In particular, as the hoop is contracted through smaller radii of curvature, the stiffness of the hoop is expected to increase dramatically. This increased stiffness prevents the hoop from being contracted more tightly, and is expected to result in a delivery profile too large to permit use of the device in critical regions of the body, such as the smaller coronary arteries, carotid arteries, and cerebral vasculature.

In view of the foregoing disadvantages of previously known apparatus and methods, it would be desirable to provide an integrated vascular device with a thrombectomy element and a vascular filter that overcomes such disadvantages of previous vascular filters while simultaneously removing thrombus.

It also would be desirable to provide a vascular device that is capable of being contracted to a small delivery profile, thus permitting use of the device in small vessels.

It further would be desirable to provide a vascular device that is capable of being contracted to a sufficiently small profile that it may be retrieved using the guide wire lumen of previously known treatment devices, and without the need for specialized delivery catheters.

It still further would be desirable to provide a vascular device that reduces the risk of emboli released during thrombectomy from escaping from the device when the device is collapsed and removed.

SUMMARY OF THE INVENTION

In view of the foregoing, it is an object of the present invention to provide a vascular device that overcomes disadvantages of previously known thrombectomy/ embolectomy devices and vascular filters, and employs few components.

It also is an object of this invention to provide a vascular device that is capable of being contracted to a small delivery profile, thus permitting use of the device in small vessels.

It is a further object of the present invention to provide a vascular device that is capable of being contracted to a sufficiently small profile that it may be retrieved using the guide wire lumen of previously known treatment devices, and without the need for specialized delivery catheters.

It is another object of this invention to provide a vascular device that reduces the risk of emboli or thrombus removed from the vessel wall escaping from the device when the device is collapsed and removed.

These and other objects of the present invention are accomplished by providing an integrated vascular device having a thrombectomy element and a vascular filter. The vascular filter comprises a blood permeable sac affixed at its perimeter to a support hoop having an articulation region. The support hoop is attached in a distal region of an elongated member, such as a guide wire, and supports a proximally-oriented mouth of the sac when the filter is deployed in a vessel. In accordance with the principles of the present invention, the support hoop includes one or more reduced-thickness articulation regions that enable the support hoop to be contracted to very small radii of curvature without the problems of increased stiffness and kinking of previously known filters.

The support hoop preferably has a curved profile that prevents the articulation region, when folded, from damaging the wall of the vessel. This feature also permits the device to effectively contact the walls of the vessel and reduce emboli or thrombus removed from the vessel wall from bypassing the sac. The articulation region when combined with a support hoop having a curved profile, causes the sides of the support hoop to fold inwards towards one-another when the vascular device is collapsed into a sheath for removal. This in turn closes the mouth of the sac and reduces the potential for emboli or thrombus to be released from the vascular device during removal.

Advantageously, use of an articulation region permits the vascular filter of the present invention to be contracted to very small diameters, thereby enabling the use of delivery catheters having diameters as small as 3 Fr. Moreover, the vascular filter of the present invention may be retracted within the guide wire lumen of conventional treatment devices, such as angioplasty catheters and stent delivery systems, thereby obviating the need to re-insert a specialized delivery catheter to remove the integrated vascular device.

The thrombectomy element of the integrated vascular device of the present invention preferably is attached to the elongated member proximal to the vascular filter, or may comprise a separate catheter. In a preferred embodiment, the thrombectomy element is similar in construction to the vascular filter, and may be retracted independently. Alternatively, the thrombectomy element may be any conventional atherectomy device used in conjunction with the vascular filter and may be advanced and retracted either in conjunction or independently of the vascular filer.

Methods of using the integrated vascular device of the present invention are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 1A and 1B are, respectively, a side sectional of a previously known vascular filter contracted within a delivery sheath and an end view of that vascular device deployed in a vessel;

FIGS. 2A and 2B are, respectively, a perspective view of a vascular filter constructed in accordance with the principles of the present invention in a deployed state, and a detailed view of the articulation region of the device of FIG. 2A;

FIG. 3 is a perspective view of the vascular filter of the present invention in a folded configuration, prior to removal;

FIG. 4 is a plan view of the vascular filter of FIG. 2A;

DETAILED DESCRIPTION OF THE INVENTION

Figure 5A:
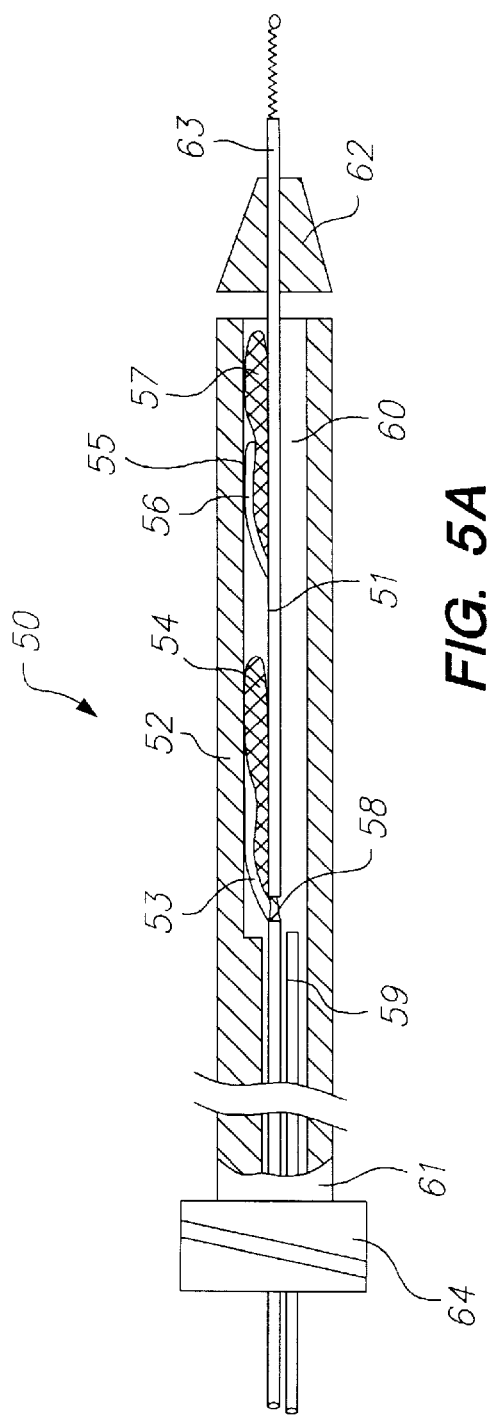
FIGS. 5A–5B are, respectively, side-sectional views depicting the integrated vascular device of the present invention disposed within a delivery sheath, and in a deployed state.

Referring to FIGS. 1A and 1B, some of the disadvantages associated with previously known vascular filters, such as the emboli filters described in the above-mentioned International Publication WO 98/39053, are described. The vascular filter comprises guide wire 10 having hoop 12 coupled to its end. Filter sac 14 is affixed to hoop 12, so that when delivery catheter 16 is retracted proximally and guide wire 10 is held stationary, hoop 12 radially expands to contact the walls of a vessel.

As described hereinabove, one difficulty with such vascular filters is that the hoop used to support the filter sac experiences increased stiffness when contracted to small diameters, i.e., due to the sharp directional change at the tip of the hoop, thereby limiting the minimum delivery profile achievable for such instruments. Although this effect may be reduced by decreasing the thickness of the wire employed in hoop 12, at the point at which the wire becomes sufficiently thin to accommodate the bending stresses, the wire is too thin to effectively radially expand and urge the filter sac into engagement with the vessel wall.

On the other hand, as shown in FIGS. 1A and 1B, the bending stresses imposed upon the hoop of such previously known devices, if drawn within a delivery catheter, may be sufficiently high to result in the formation of kink 18 at the tip of the hoop. This "kinking" effect becomes more severe in sheaths having a small inner diameter. Thus, for example, applicant has observed that when sheaths having inner diameters of 0.035" or smaller are used, a hoop of nitinol or multi-strand nitinol cable having a diameter of 0.0055 inches will form kink 18. Kink 18 in turn may apply relatively high localized pressure and friction against wall 17 of sheath 16, thereby making the vascular filter difficult to deploy. In particular, the kink may impale wall 17 of delivery sheath 16 and may make it difficult or impossible to deploy the vascular filter, especially in tortuous anatomy.

In addition, when the filter is subsequently deployed in vessel V, as shown in FIG. 1B, kink 18 may deform the pre-formed shape of hoop 12, impairing the ability of the filter to seal against the walls of vessel V. This may in turn lead to the presence of gaps G between the perimeter of the hoop and the vessel wall, depending upon the severity of the kink. Consequently, emboli may pass through the gaps with antegrade flow and significantly reduce the efficacy of the filter. Additionally, kink 18 may be sufficiently sharp to damage or dissect the wall of vessel V when the filter is deployed.

The vascular filter of the integrated vascular device of the present invention solves the above-described disadvantages, providing a vascular filter with a self-expanding support hoop that is sufficiently thick to radially expand and urge a blood permeable sac into engagement with the vessel wall, but which includes an articulation region that overcomes the problems associated with kinking. In particular, the vascular filter includes a reduced thickness articulation region and a pre-formed curved profile that avoids the difficulties of previously known systems while providing a high degree of efficacy in capturing emboli or thrombus, and ease of deployment and retrieval.

Referring now to FIGS. 2A and 2B, vascular filter 20 of the integrated vascular device constructed in accordance with the principles of the present invention comprises guide wire 22, support hoop 24 having articulation region 26, and blood permeable sac 28 affixed to support hoop 24. Sac 28 is coupled to support hoop 24 so that the support hoop 24 forms an opening for the sac. Support hoop 24 preferably is connected to guide wire 22 near distal end 23 of the guide wire.

Sac 28 preferably is constructed of a thin, flexible biocompatible material, such as polyethylene, polypropylene, polyurethane, polyester, polyethylene tetraphlalate, nylon or polytetrafluoroethylene, or combinations thereof, and includes openings or pores 30 that permit blood cells to pass through the sac substantially unhindered, while capturing any larger emboli that may be released during a procedure such as angioplasty or stent placement. In a preferred embodiment, sac 28 has openings or pores 30 in a range of about 20 to 400 microns in diameter, and more preferably, about approximately 80 microns. These pores sizes will permit red blood cells (which have a diameter of approximately 5 microns) to easily pass through the sac. If sac 28 comprises a woven material, such as formed from the above-mentioned polymers, the pore size of the sac may be determined as a function of the pattern and tightness of the weave.

Support hoop 24 comprises a hoop having a circular or rectangular cross-section that is formed of a super-elastic material, such as a nickel-titanium alloy ("nitinol"). During deployment and retrieval of vascular filter 20, described hereinafter, support hoop 24 folds in half and collapses to fit within a small diameter delivery sheath. When vascular filter 20 is in a deployed state, as depicted in FIG. 2A, support hoop 24 resumes its pre-formed shape. Support hoop 24 preferably comprises nitinol wire, although it may also be formed from a multistrand nitinol cable, or other super-elastic material.

In accordance with the principles of the present invention, support hoop 24 includes reduced-thickness articulation region 26, illustratively, disposed opposite to point 32 at which support hoop 24 is affixed to guide wire 22. Support hoop 24 is pre-formed to form a structure having curved regions 34, so that articulation region 26 preferably is disposed in a portion of the support hoop that is approximately parallel to a vessel wall when vascular filter 20 is deployed. As depicted in FIG. 2B, articulation region 26 includes a region having reduced thickness $t_1$ compared to thickness t of the remainder of support hoop 24. Articulation region 26 and curved regions 34 enable support hoop 24 to fold with a pre-determined shape when vascular filter 20 is collapsed to a contracted state for delivery or retrieval.

In FIG. 2B, articulation region 26 is depicted as a localized reduction in the thickness of support hoop 24, as may be achieved, for example, using conventional grinding or etching processes, or electropolishing. Alternatively, support hoop 24 may be continuously tapered along its circumference, so that articulation region 26 results from a more gradual reduction in the wall thickness of the support hoop. Tapering support hoop 24 may permit greater flexibility in the vicinity of articulation region 26, thus enabling support hoop 24 to fold more easily at the articulation region. Such tapering of the thickness of the support hoop along a portion of its circumference also may reduce the potential for stress-induced fracture typically associated with abrupt changes in diameter.

In a preferred embodiment of vascular filter 20 of the integrated vascular device of the present invention, vascular filter 20 easily fits within a delivery sheath having an inner diameter of 0.033", and more preferably, may be used with a delivery sheath having an inner diameter as small as 0.026". The deployed diameter of support hoop 24 preferably is approximately 7 mm, while guide wire 22 preferably has a diameter of 0.014", and tapers at its distal end. The distal end of guide wire 22 also may be tipped with a spring section, or coil tip, such as are per se known.

Support hoop 24 preferably is constructed of 0.0055" nitinol wire tapered (by a grinding process) to 0.0025" at articulation region 26. Specifically, articulation region 26 preferably consists of a length about 0.05" long and having a diameter of 0.0025", coupled on either side to curved regions 34. Each of curved regions 34 includes of a length of wire that is tapered from a diameter of 0.055" to a diameter of 0.0025" over a length of about 0.025". Support hoop 24 also may include radiopaque features, such as gold or platinum bands 33, spaced at intervals around the circumference of support hoop 24.

With respect to FIGS. 3 and 4, additional features of vascular filter 20 are described. FIG. 3 depicts vascular filter 20 of FIG. 3 in a contracted state, while FIG. 4 provides an exaggerated view of the directional change in support hoop 24 caused by the presence of curved regions 34. In particular, FIG. 4 illustrates how, in a preferred embodiment, curved regions 34 orient articulation region 26 in a direction parallel to the axis of guide wire 22.

Advantageously, use of articulation region 26 and the curved profile of support hoop 24 introduced by curved regions 34 also cause support hoop 24 to fold in half during retrieval. As shown in FIG. 3, support hoop 24 folds in half, effectively closing the mouth of blood permeable sac 28 and preventing the escape of collected emboli or thrombus. This feature also may permit the use of a smaller or shallower sac than would not otherwise be possible, without increasing the risk of material escaping from the filter when the sac is collapsed for retrieval. Use of a smaller or shallower sac also enables vascular filter 20 to be delivered in a smaller delivery sheath, having an inner diameter as small as 0.026" for the preferred embodiment.

In a preferred embodiment, the thrombectomy element of the integrated vascular device of the present invention is similar in construction to vascular filter 20 described above, and is connected to guide wire 22 proximal to vascular filter 20. The thrombectomy element may be retracted independently of vascular filter 20. Alternatively, the thrombectomy element may be disposed on a separate catheter.

Figure 5B:
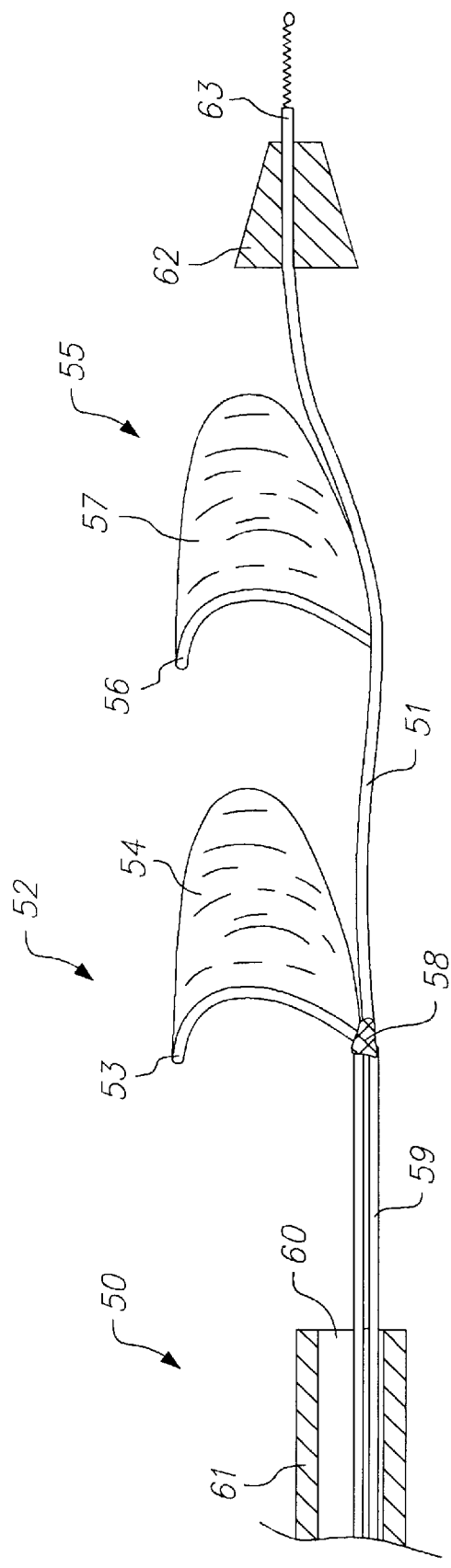

Referring now to FIGS. 5A and 5B, the integrated vascular device of the present invention is described. Integrated vascular device 50 comprises guide wire 51, thrombectomy element 52 including support hoop 53 and blood permeable sac 54, and vascular filter element 55 including support hoop 56 and blood permeable sac 57. Filter hoop 56 is attached to guide wire 51 while thrombectomy hoop 53 is attached to ring 58. Ring 58 is attached to pull wire 59 and has a bore through which guide wire 51 passes. Ring 58 therefore acts as a linear bearing and allows thrombectomy hoop 53 to be moved by pull wire 59 independently of guide wire 51. Alternatively, thrombectomy element 52 may omit sac 54 and simply comprise a wire hoop; in this case severed thrombus is captured by vascular filter 55.

In FIG. 5A, support hoops 53 and 56 and blood permeable sacs 54 and 56 are contracted to a delivery state within lumen 60 of delivery sheath 61. Delivery sheath 61 includes nose cone 62 affixed to distal region 63 of guide wire 51. In FIG. 5B, integrated vascular device 50 is shown deployed in a vessel. As illustrated in FIG. 5B, vascular filter 55 expands to engage the perimeter of the vessel and prevent thrombus from bypassing the blood permeable sac, while thrombectomy element 52 engages the vessel wall proximal of vascular filter 55. As described hereinbelow, proximal movement of thrombectomy device 52 scrapes thrombus from the wall of the vessel when pull wire 59 pulls ring 58 and support hoop 53 proximally.

Figure 6A:
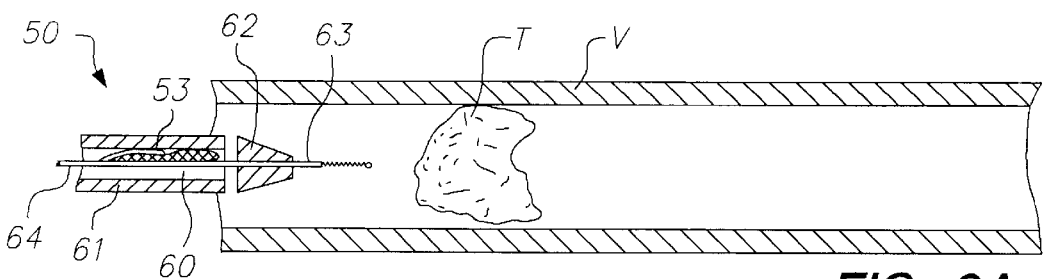
FIGS. 6A–6E are side-sectional views depicting a method of deploying, using and retrieving the integrated vascular device of the present invention.

Referring now to FIGS. 6A–6E, an illustrative method of using the integrated vascular device of the present invention for thrombectomy is described. In FIG. 6A, guide wire 51 is manipulated into position proximal to thrombus T within vessel V using well-known percutaneous techniques. Vascular device 50 of FIGS. 5A and 5B is disposed in its contracted delivery state within the distal end of delivery sheath 61 and the delivery sheath is advanced through the vessel using distal end 63 of guide wire 51. The sides of support hoops 53 and 56 are folded together and become elongated when drawn within delivery sheath 61, as described with respect to vascular device 20 of FIGS. 2–4.

Figure 6B:
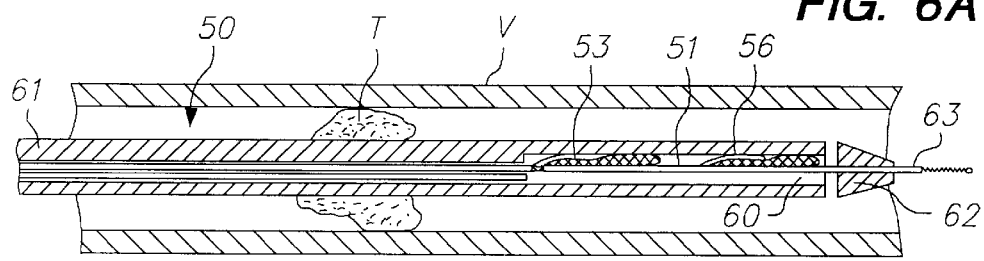

With respect to FIG. 6B, once delivery sheath 61 is disposed at the desired location proximal to thrombus T within a patient's vessel V, such as a coronary artery or carotid artery, for example, based on the position of, for example, radiopaque bands under a fluoroscope, integrated vascular device 50 is advanced through thrombus T. Distal end 63 of guide wire 51 is advanced through the lesion, then nose cone 62 gradually increases the diameter of the void within thrombus T so that the remainder of delivery sheath 61 can be advanced far enough that thrombectomy element 52 (still within delivery sheath 61) is located distal to thrombus T.

Figure 6C:
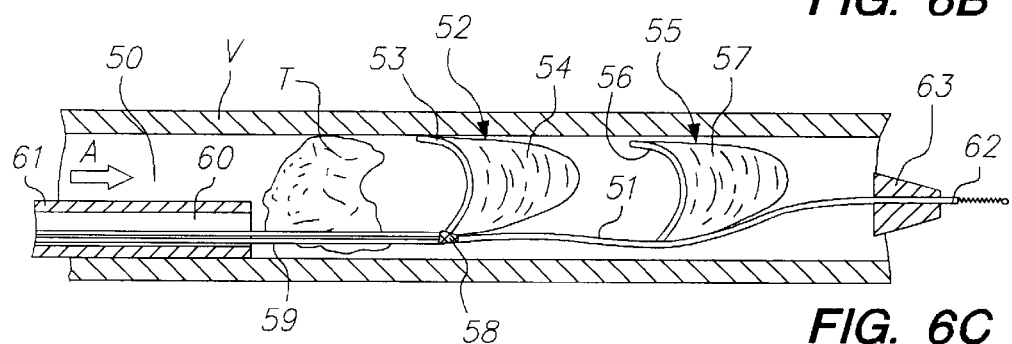

With integrated vascular device 50 in position, guide wire 51 is held stationary while delivery sheath 61 is retracted proximally, as seen in FIG. 6C. Alternatively, delivery sheath 61 may be held stationary while guide wire 51 is advanced. In either case, when vascular device 50 is no longer confined within delivery sheath 61, support hoops 53 and 56 expand to seal against the walls of the vessel V and deploy blood permeable sacs 54 and 57, respectively. Blood continues to flow through vessel V in direction A, impeded only by thrombus T.

Figure 6D:
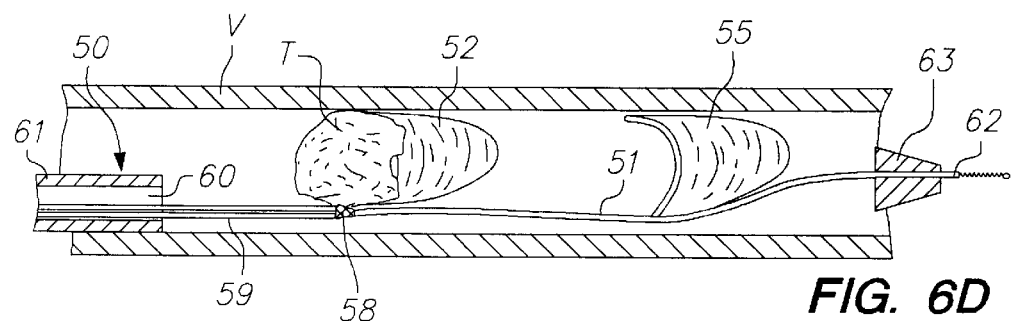

In FIG. 6D, once vascular device 50 is deployed in vessel V, thrombus T is removed in the following manner. Vascular filter support hoop 53 is rigidly attached to guide wire 51, while thrombectomy support hoop 53 is attached to pull wire 59 via ring 58. Thrombectomy element 52 then is retracted proximally to scrape along the wall of the vessel V by motion at the proximal end of pull wire 59. Thrombus T, located proximal to thrombectomy element 52, is excised so that it is captured in blood permeable sac 54 during the retraction.

Figure 6E:
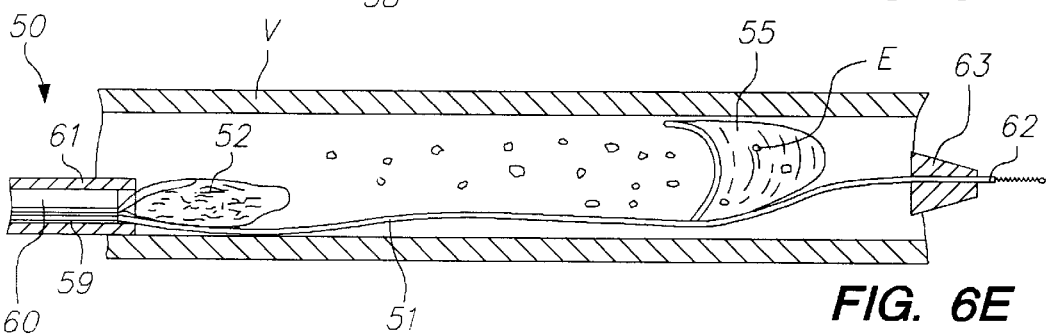

With respect to FIG. 6E, once thrombus T has been captured within sac 54, pull wire 59 is pulled proximally to cause the sides of thrombectomy support hoop 53 to collapse together to close the mouth of sac 28 (see FIG. 3). Additional proximal retraction of pull wire 59 causes support hoop 53 and sac 54 to enter within lumen 60 of delivery sheath 61, restoring normal blood flow to vessel V. Meanwhile, vascular filter 55 is in a position distal to thrombectomy element 52 to trap emboli E, i.e., pieces of plaque dislodged from either thrombus T or the walls of vessel V by thrombectomy element 52. Once any emboli E have been collected, filter hoop 56 and sac 57 are retracted into delivery sheath 61 by motion at the proximal end of guide wire 51, in a manner similar to the retraction of hoop 53 and sac 54. Once guide wire 51 has been fully retracted and nose cone 62 at the distal end 63 of guide wire 51 is again in contact with delivery sheath 61, the delivery sheath is withdrawn with integrated vascular device 50, the trapped thrombus T and any trapped emboli E.

Advantageously, the compliant design of integrated vascular device 50 permits the device to be contracted to its delivery state within the guide wire lumen of conventional previously known interventional devices. Accordingly, unlike previously known vascular devices, which require removal of the interventional device followed by re-insertion of a specially designed catheter to retrieve the vascular device, the system of the present invention reduces the time, effort and trauma of this additional step. Instead, the vascular device may be readily closed and retrieved upon completion of the interventional procedure.

Figure 7A:
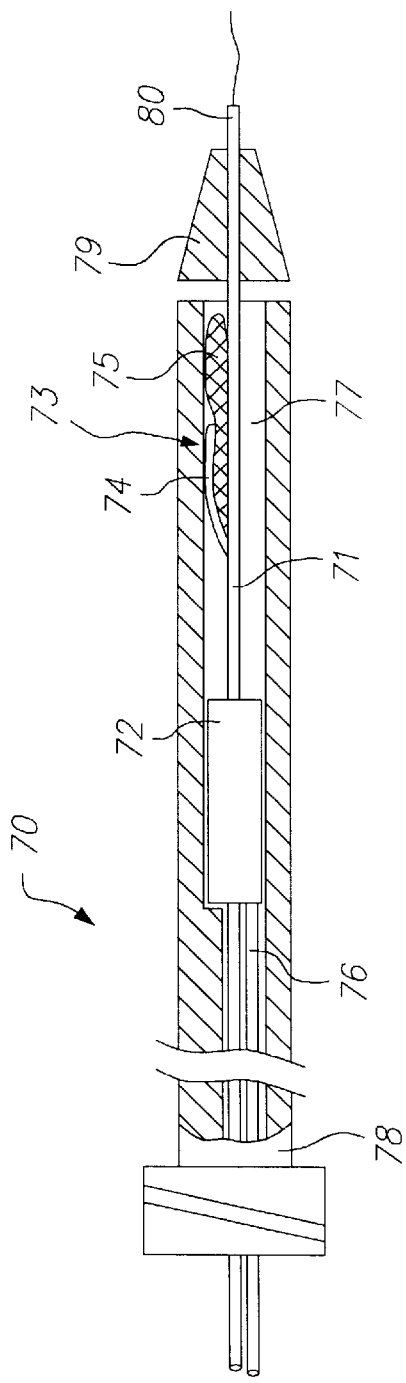
FIGS. 7A–7B are, respectively, side-sectional views depicting an alternative embodiment of the integrated vascular device disposed within a delivery sheath, and in the deployed state.
Figure 7B:
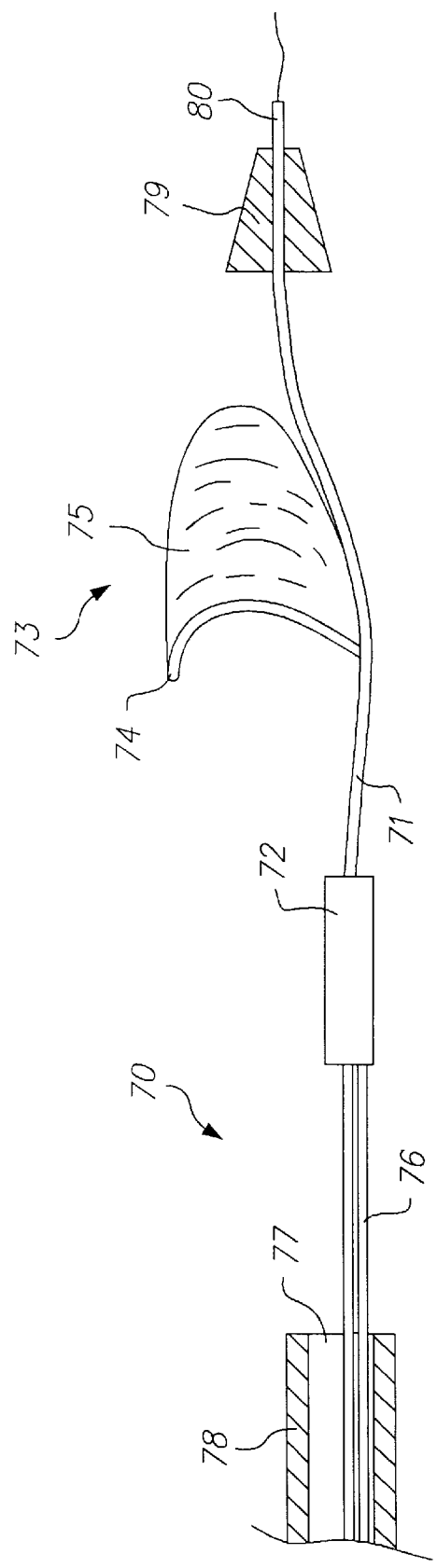

Referring now to FIGS. 7A and 7B, an alternative embodiment of the integrated vascular device of the present invention is described. Integrated vascular device 70 comprises guide wire 71, thrombectomy element 72 and vascular filter 73 including support hoop 74 and blood permeable sac 75. Filter hoop 74 is attached to guide wire 71, while thrombectomy element 72 is disposed to slide along guide wire 71. Alternatively, thrombectomy element 72 may be disposed on a separate catheter element that extends either through lumen 77 of delivery sheath 78 or is separately disposed proximal to vascular filter 73.

FIG. 7A shows thrombectomy element 72 and vascular filter 73 contracted in a delivery state within lumen 77 of delivery sheath 78. Delivery sheath 78 includes nose cone 79 affixed to distal region 80 of guide wire 71. In FIG. 7B, integrated vascular device 70 is shown in the deployed state. Thrombectomy element 72 may comprise any of a family of known thrombectomy, atherectomy, or, alternatively, drug delivery devices suitable for use in conjunction with vascular filter 73.

Specifically, thrombectomy element 72 may comprise any of: a rotary ablation device, such as described in U.S. Pat. Nos. 4,867,156 to Stack et al., 4,990,134 to Auth, and 5,314,407 to Auth et al.; an atherectomy technology, such as described in U.S. Pat. Nos. 5,181,920 to Mueller et al., and 5,074,841 to Ademovic et al.; or a balloon embolectomy technology, such as described in U.S. Pat. Nos. 3,923,065 to Nozick et al., 5,769,871 to Mers Kelly et al., 5,192,290 to Hilal, 5,112,347 to Taheri, and 4,030,503 to Clark III. All of the foregoing patents are incorporated herein by reference. Thrombectomy element 72 may alternatively comprise a wire loop or ring such as alternatively described for the embodiment of FIGS. 5A and 5B, a laser ablation device, a chemical flushing system, etc.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. Apparatus suitable for performing thrombectomy comprising:

an elongated member having a distal region;

a support hoop attached to the distal region, the support hoop having a reduced-thickness articulation region, the hoop attached to the elongated member;

a blood permeable sac affixed to the support hoop so that the hoop forms a mouth of the blood permeable sac;

a thrombus removal element disposed proximal of the support hoop, the thrombus removal element movable in a proximal direction independent of the elongated member.

2. The apparatus of claim 1, wherein the thrombus removal element comprises a second support hoop with blood permeable sac.

3. The apparatus of claim 2, wherein the second support hoop is slidably disposed on the elongated member.

4. The apparatus of claim 1, wherein the blood permeable sac comprises a biocompatible material.

5. The apparatus of claim 4, wherein the biocompatible material comprises a material chosen from a list consisting of polyethylene, polypropylene, polyester, polyurethane and nylon.

6. The apparatus of claim 1, wherein the blood permeable sac comprises a woven material having a plurality of pores, the pores having a size determined by a weave pattern of the woven material.

7. The apparatus of claim 6, wherein each one of the plurality of pores has a diameter in a range of 20 to 400 microns.

8. The apparatus of claim 1, wherein the support hoop comprises a super-elastic material.

9. The apparatus of claim 8, wherein the super-elastic material comprises a nickel-titanium alloy.

10. The apparatus of claim 1, wherein the support hoop comprises a wire having a thickness that tapers to a minimum thickness at the articulation region.

11. The apparatus of claim 1, wherein the apparatus has a deployed state, wherein the hoop engages an interior wall of a patient's vessel, and a delivery state, wherein the apparatus has a contracted configuration to permit insertion within a delivery sheath.

12. The apparatus of claim 11, wherein the support hoop folds at the articulation region when the apparatus is contracted to the delivery state.

13. The apparatus of claim 11, wherein thrombus is excised or ablated by the thrombus removal element.

14. The apparatus of claim 11, wherein the mouth of the blood permeable sac is closed when the apparatus is in the contracted configuration, thereby preventing emboli from escaping from the blood permeable sac.

15. The apparatus of claim 12 wherein opposite sides of the support hoop close towards one another when the apparatus is contracted to its contracted configuration.

16. The apparatus of claim 1, wherein the support hoop comprises a radiopaque band.

17. The apparatus of claim 1 further comprising:

a nose cone disposed on the distal region of the elongated member distal to the support hoop;

and a delivery sheath having a lumen for accepting the elongated member, thrombus removal element, support hoop and blood permeable sac.

18. A method of trapping thrombus and/or emboli during a medical procedure, the method comprising:

providing apparatus comprising an elongated member having a distal region, a support hoop having an articulation region coupled to the distal region of the elongated member, a blood permeable sac affixed to the support hoop so that the hoop forms a mouth of the blood permeable sac, and a thrombus removal element disposed proximal to the support hoop;

positioning the apparatus in a contracted delivery state within a delivery sheath;

advancing the delivery sheath to a desired location within a patient's vessel; and withdrawing the delivery sheath to expand the apparatus to a deployed state wherein the support hoop seals against the vessel wall, and the thrombus removal element is configured to excise or ablate the thrombus.

19. The method of claim 18, wherein advancing the delivery sheath to a desired location within a patient's vessel comprises advancing the delivery sheath through an interior lumen of a catheter so that a distal region of the delivery sheath is disposed distal to the lesion.

20. The method of claim 18 further comprising retracting the apparatus within the delivery sheath by folding the support hoop at the articulation region to close the mouth of the blood permeable sac.

21. The method of claim 20, wherein the thrombus removal element comprises an additional support hoop and blood permeable sac.

22. The method of claim 21, wherein the additional support hoop is slidably disposed on the elongated member, the method further comprising sliding the additional support hoop proximally to excise thrombus from the vessel by scraping against the vessel wall.

* * * * *